(12) United States Patent
Senthilkumar et al.

(10) Patent No.: US 7,361,761 B2
(45) Date of Patent: Apr. 22, 2008

(54) PROCESS FOR THE PREPARATION OF BISPHOSPHONIC ACID

(75) Inventors: Udayampalayam P. Senthilkumar, Tamilnadu (IN); Thangavel Arulmoli, Tamilnadu (IN); Venu S. Lakshmipathi, Tamilnadu (IN); Siripragada M. Rao, Tamilnadu (IN)

(73) Assignee: Orchid Chemicals & Pharmaceuticals Ltd., Tamilnadu (IN)

( * ) Notice: Subject to any disclaimer, the term of this patent is extended or adjusted under 35 U.S.C. 154(b) by 0 days.

(21) Appl. No.: 11/522,908

(22) Filed: Sep. 19, 2006

(65) Prior Publication Data

US 2007/0066569 A1    Mar. 22, 2007

(51) Int. Cl.
C07D 471/04    (2006.01)
C07D 233/58    (2006.01)
C07F 9/28      (2006.01)

(52) U.S. Cl. .................. 546/23; 562/13; 548/112; 546/22

(58) Field of Classification Search .............. 562/13; 548/112; 546/22, 23
See application file for complete search history.

(56) References Cited

U.S. PATENT DOCUMENTS

| 4,407,761 A | 10/1983 | Blum et al. |
| 4,705,651 A | 11/1987 | Staibano |
| 4,922,007 A | 5/1990 | Kieczykowski et al. |
| 5,019,651 A | 5/1991 | Kieczykowski |
| 5,908,959 A | 6/1999 | Kubela et al. |

FOREIGN PATENT DOCUMENTS

DE    2 130 794    1/1973

OTHER PUBLICATIONS

Kieczykowski et al., "Preparation of (4-Amino-1-Hydroxybutylidene) bisphosphonic Acid Sodium Salt, MK-217 (Alendronate Sodium). An Improved Procedure for the Preparation of 1-Hydroxy-1,1-bisphosphonic Acids," J. Org. Chem., 60, pp. 8310-8310, 1995.

Primary Examiner—Charanjit S. Aulakh
(74) Attorney, Agent, or Firm—Oliff & Berridge PLC

(57) ABSTRACT

The present invention is to relate an improved process using anisole as solvent for the preparation of compound of formula (I) and its pharmaceutically acceptable salts thereof.

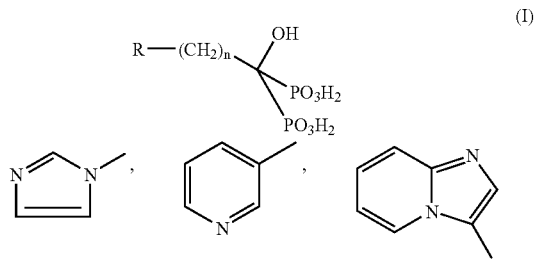

wherein R represents —$NR_1R_2$, or a group
n=1, 2, 3, 4 and 5, where $R_1$ and $R_2$ may be same or different and independently represents hydrogen, or $C_{1-6}$ alkyl.

6 Claims, No Drawings

PROCESS FOR THE PREPARATION OF BISPHOSPHONIC ACID

FIELD OF THE INVENTION

The present invention relates to an improved process for the preparation of bisphosphonic acid of formula (I) and its pharmaceutically acceptable salts thereof,

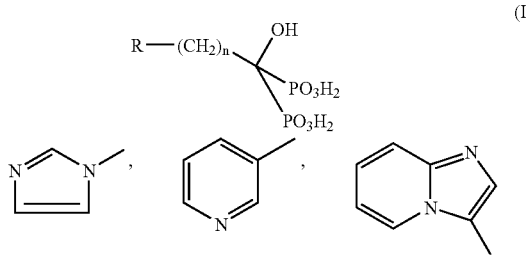

Wherein R represents —$NR_1R_2$, n=1, 2, 3, 4 and 5, where $R_1$ and $R_2$ independently represents hydrogen, $C_{1-6}$ alkyl.

BACKGROUND OF THE INVENTION

The bisphosponates, which are salts of bisphosphonic acids, are an important class of medicaments useful in the treatment of bone disorders such as Paget's disease and osteoporosis. The sodium salt of risedronic acid, sodium salt of pamidronic acid, sodium salt of alendronic acid are the examples of pharmaceutically useful bisphosphonates.

The bisphosphonates are derived from the corresponding bisphosphonic acids. Several methods have been reported for preparing 1-hydroxy-1,1-bisphosphonic acids. The syntheses are based on reacting a carboxylic acid with a mixture of phosphorous acid and one of the following phosphorous halides: phosphorous trichloride ($PCl_3$), phosphorous oxychloride ($POCl_3$), phosphorous pentachloride ($PCl_5$), phosphorous tribromide ($PBr_3$), phosphorous oxybromide ($POBr_3$) or phosphorous pentabromide ($PBr_5$), then quenching the reaction mixture with water or a nonoxidizing aqueous acid, followed by heating to hydrolyze the phosphorous intermediates to the final product.

The preparation of 3-amino-1-hydroxypropane-1,1-diphosphonic acid by reaction of beta.-alanine with a mixture of phosphorous trichloride and phosphorous acid in the presence or absence of an organic diluent is known from the German Patent Specification No. 21 30 794. However, yellow-red by-products in the form of amorphous phosphorus-oxygen compounds of unknown structure are formed in this reaction and their separation, particularly in the presence of chlorobenzene, is very costly. Another factor to be considered in the large scale preparations is the dangerously high flammability of these phosphorus compounds In U.S. Pat. No. 4,407,761 the preparation of 4-amino-1-hydroxybutylidene-1,1-biphosphonic acid besides other bisphosphonic acids are described. When using this procedure, a semisolid sticky non-stirrable mass develops which prevents smooth heat transfer. The described process might be suitable for-laboratory preparations, however for industrial production it is not acceptable.

In U.S. Pat. No. 4,705,651 a similar procedure is followed with different molar ratios and although some improvements were achieved, it is still unsuitable for industrial scale up.

U.S. Pat. Nos. 4,922,007, 5,019,651 and J. Org. Chem. 1995, 60, 8310-8312 reported that the solidification problem has been solved by using methanesulfonic acid to solubilize the reaction components and keep them fluid throughout, by the use of methanesulfonic acid the fluidity problems were solved however another serious safety problem surfaced. A reaction between methanesulfonic acid and phosphorus trichloride is exothermic and at certain point becomes uncontrollable, U.S. Pat. No. 5,908,959 also describes the preparation of 4-amino-1-hydroxybutylidene-1,1-biphosphonic acid or salts.—thereof. The reaction is carried out in poly(alkylene glycol) as a diluent, which solubilizes the reaction components, however still when the reaction mixture is decomposed with water, an agitation problem occurs. The viscous reaction mixture must be transferred into the water. To facilitate this, viscosity problem is solved by the addition of toluene. When using toluene, a safety problem arises and also an additional separation step is needed.

The present invention solves the problems by allowing the reaction to remain stirrable using anisole as solvent, and making commerical manufacturing possible thus allowing complete conversion of the carboxylic acid providing excellent yields and purity of the formula (I).

OBJECTIVES OF THE INVENTION

The main objective of the present invention is to provide an improved process using anisole as solvent for the preparation of compound of formula (I) and its pharmaceutically acceptable salts thereof.

Another objective of the present invention is to provide a process for the preparation of compound of formula (I) and its pharmaceutically acceptable salts thereof, which would be easy to implement on commercial scale, which can avoid the use of hazardous chemicals like methane sulfonic acid, chloro benzene and toluene.

Still another objective of the present invention is to provide a process for the preparation of compound of formula (I) and its pharmaceutically acceptable salts in good yield and high purity.

SUMMARY OF THE INVENTION

Accordingly, the present invention provides an improved process for the preparation of bisphosphonic acid of formula (I) and its pharmaceutically acceptable salts thereof,

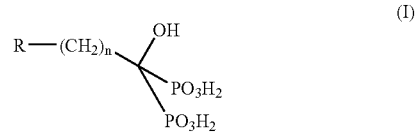

where R is as defined above. The method of making a bisphosphonic acid comprising the steps of i) reacting carboxylic acid of formula (II) with a mixture of phosphorous acid and $PCl_3$ in the presence of solvent anisole at a temperature of about 100-115° C., ii) Combining the reaction mixture with water, whereby an aqueous and a non-aqueous phase are formed, iii) separating the aqueous layer and neutralize with sodium hydroxide solution, iv) combining the aqueous phase with methanol whereby a suspension comprising bisphosphonic acid is formed, and
v) isolating the compound of formula (I) or salts thereof.

The process is shown in the scheme given below

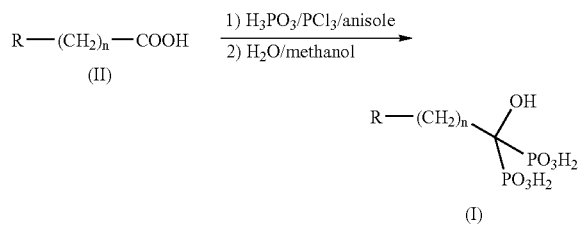

DETAILED DESCRIPTION OF THE INVENTION

In an embodiment of the present invention the carboxylic acid of formula (II) is selected from 4-aminobutanoic acid, (3-pyridyl) ethanoic acid, (1-imidazoyl) ethanoic acid, N-(n-pentyl)-N-methyl-3-aminopropanoic acid, 2(imidazo[1,2-a]pyridin-3-yl)ethanoic acid, 3-aminopropanoic acid and 6-aminohexanoic acid, and the hydrochlorides thereof.

In another embodiment of the present invention the phosphonating reagent selected from a mixture of phosphorous acid and a halophosporous compound selected from phosphorous trichloride ($PCl_3$), phosphorous pentachloride ($PCl_5$), phosphorous tribromide ($PBr_3$), phosphorous pentabromide ($PBr_5$), Phosphorous oxybromide ($POBr_3$), phosphorous oxychloride ($POCl_3$) and the like or mixtures thereof.

In yet another embodiment of the present invention the bisphosphonation reaction generally takes place at a temperature of from 45° C. to 125° C., preferably in the range of 100-115° C.

In yet another embodiment of the present invention the quenching temperature is in the range of 50° C. to reflux and preferably at the reflux temperature of about 105-115° C.

In another embodiment compound of formula (I) is further converted to pharmaceutically acceptable salts such as potassium, sodium, calcium or magnesium and the like by conventional methods.

The present invention is exemplified by the following example, which is provided for illustration only and should not be construed to limit the scope of the invention.

EXAMPLE 1

Preparation of 4-amino-1-hydroxybutylidene-1,1-biphosphonic acid mono sodium salt trihydrate Step-(I)—Preparation of Alendronic Acid 100 gm (0.97 mol) of 4-Aminobutyric acid (GABA), 119.3 gm (1.45 mol) of phosphorous acid and 600 ml of anisole are charged in a dry and nitrogen flushed 2 lt flask fitted a mechanical stirrer, a thermometer pocket, an addition funnel and a reflux condenser that circulated with chilled water. The mixture is heated up to 60-70° C. and then charged slowly phosphorous trichloride 333.0 gm (2.42 mol) under vigorous stirring in 40-45 minutes at 60-70° C. The reaction mixture is heated to 100-105° C. and stirred for 5 hrs until the HCl gas evaluation is completely stopped and then the mass is allowed to cool. The solvent is separated and water (400 ml) is added slowly under stirring. Heating and stirring started again and refluxed the mass for 5-6 hrs at 110-115° C. It is then cooled to 28-30° C. The trapped solvent and aqueous phases are separated. The aqueous phase is cooled to 20-25° C. and pH of the solution is adjusted to 1.8 by using caustic lye solution. To this solution, methanol is added slowly to precipitate of the crude alendronic acid and filtered (230-250 gm).

The crude alendronic acid obtained above is taken in a 1-lt flask equipped with mechanical stirrer, a reflux condenser and deminaralized water (500 ml) is charged in to it, heated the mixture to 70° C. under stirring and then the pH of the suspension is adjusted to 1.8 using conc. hydrochloric acid. The suspension is heated to 80-85° C. under stirring and stirred for 3-4 hrs and then cooled gradually to 28-30° C. in 2 hrs. The pH of the suspension is 1.7-2.0 and aged for 1 hr at 28-30° C. The product is collected by filtration. The yield of alendronic acid after drying at 60-65° C. under vacuum until constant weight is 166.9 gm (~90%).

Step (II)—Preparation of Sodium Salt as Trihydrate:

100 gm of 4-amino-1-hydroxybutylidene-1,1-biphosphonic acid is suspended in 500 ml of deinoised water with vigorous stirring at 30 to 70° C. The pH of the suspension is adjusted to 4.4-4.6 by using 30% w/w aqueous solution of sodium hydroxide to form a clear solution. The clear solution is filtered through a filter medium to remove fine foreign particles if any and the filtered solution is aged overnight at 2-4° C. The product crystallized is filtered, washed with 50 ml cold deminaralized water and then dried to yield 105.3 gm of alendronate sodium trihydrate. The yield of the product on the basis of 4-amino butyric acid is 1.76 w/w.

What is claimed is:

1. A process for the preparation of bisphosphonic acid of the formula (I) or its pharmaceutically acceptable salts thereof

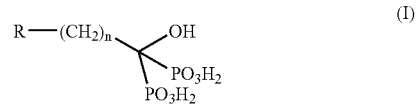

wherein R represents -$NR_1R_2$, or a group

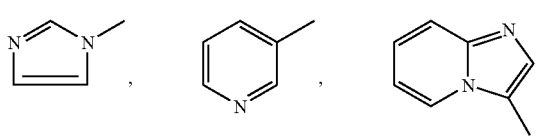

n=1, 2, 3, 4 or 5, where $R_1$ and $R_2$ may be same or different and independently represents hydrogen, or $C_{1-6}$ alkyl; said process comprising the steps of (i) reacting the carboxylic acid of formula (II)

Wherein R is defined above; with phosphorous acid and a halophosporous compound in the presence of anisole at 45-120° C., and (ii) isolating the compound of formula (I).

2. A process according to claim 1, wherein the halophosporous compound is selected from PCl₃, PCl5, PBr₃, PBr₅, POBr₃, or POCl₃.

3. A process according to claim 1, wherein said reaction is conducted at a temperature in the range of 100-150° C.

4. A process according to claim 1, wherein the pharmaceutically acceptable salt is selected from sodium, potassium, calcium or magnesium.

5. A process according to claim 1, wherein the pharmaceutically acceptable salt is sodium.

6. The process as claimed in claim 1 which is for the preparation of alendronic acid, pamidronic acid, risedronic acid, zoledronic acid, ibandronic acid, minodronic acid or neridronic acid.

* * * * *